(12) United States Patent
LoVuolo

(10) Patent No.: US 6,595,911 B2
(45) Date of Patent: Jul. 22, 2003

(54) METHOD AND DEVICE FOR ANCHOR IMPLANTATION AND SUPPORT OF BODILY STRUCTURES

(76) Inventor: Michael LoVuolo, 52 Commercial Wharf, Unit 1, Boston, MA (US) 02110

( * ) Notice: Subject to any disclaimer, the term of this patent is extended or adjusted under 35 U.S.C. 154(b) by 55 days.

(21) Appl. No.: 09/825,032

(22) Filed: Apr. 3, 2001

(65) Prior Publication Data

US 2002/0143234 A1 Oct. 3, 2002

(51) Int. Cl.$^7$ .................................................. A61F 2/02
(52) U.S. Cl. ..................... 600/30; 600/37; 128/DIG. 25
(58) Field of Search .............................. 600/29, 30, 31, 600/32, 37; 128/DIG. 25

(56) References Cited

U.S. PATENT DOCUMENTS

| | | | |
|---|---|---|---|
| 4,006,747 A | | 2/1977 | Kronenthal et al. |
| 4,172,458 A | | 10/1979 | Pereyra |
| 4,669,473 A | | 6/1987 | Richards et al. |
| 4,705,040 A | | 11/1987 | Mueller et al. |
| 4,741,330 A | * | 5/1988 | Hayhurst ...................... 128/92 |
| 4,938,760 A | | 7/1990 | Burton et al. |
| 5,013,292 A | * | 5/1991 | Lemay ......................... 600/30 |
| 5,019,032 A | * | 5/1991 | Robertson .................... 600/29 |
| 5,256,133 A | | 10/1993 | Spitz |
| 5,337,736 A | * | 8/1994 | Reddy ......................... 600/37 |
| 5,362,294 A | * | 11/1994 | Seitzinger .................... 600/37 |
| 5,562,689 A | | 10/1996 | Green et al. |
| 5,647,836 A | | 7/1997 | Blake, III et al. |
| 5,816,258 A | | 10/1998 | Jervis |
| 6,042,534 A | | 3/2000 | Gellman et al. |
| 6,053,935 A | | 4/2000 | Brenneman et al. |
| 6,059,801 A | | 5/2000 | Samimi |
| 6,334,446 B1 | * | 1/2002 | Beyar ......................... 600/37 |

* cited by examiner

Primary Examiner—James Hook
(74) Attorney, Agent, or Firm—O'Connell Law Firm

(57) ABSTRACT

A method and device for suspending, stabilizing, and/or slightly compressing a bodily structure, such as a urethrovesical junction. The device comprising a delivery needle with a trocar, a stylet for being matingly received into the delivery needle, and a support formed by an anchor toggle and elongate first and second sutures. A longitudinal slot can be disposed at the distal end of the delivery needle for allowing the sutures to protrude therefrom. The delivery needle can have a curve with the slot and a base of the trocar disposed on an inside of the curve. An aligning handle, visual and tactile orientation indicators, and depth indicators can be disposed on the delivery needle for allowing a determination of the orientation, depth, and location of the distal end of the delivery needle. A sling can be used to spread a supporting force of the sutures over a greater area.

28 Claims, 11 Drawing Sheets

METHOD AND DEVICE FOR ANCHOR IMPLANTATION AND SUPPORT OF BODILY STRUCTURES

FIELD OF THE INVENTION

The invention described herein relates generally to an anchoring member with trailing sutures and a method and device for applying and adjusting those structures to support a bodily structure of a patient, such as a female. The method and device are particularly disclosed in reference to a device and a method for suspending, stabilizing, and/or slightly compressing the female urethra, particularly the urethrovesical junction, thereby improving or maintaining urinary continence in a female patient without a need for percutaneous incision.

BACKGROUND OF THE INVENTION

Female incontinence, the inability to control the outflow of urine in women, can have a variety of causes. In roughly a third of the women afflicted, urinary incontinence is the result of intrinsic sphincter deficiency (ISD) wherein the urethral sphincter does not coapt properly. In approximately a second third of the women experiencing urinary incontinence, it is the result of hypermobility wherein the muscles and lateral attachments adjacent to the bladder neck relax such that the bladder neck and proximal urethra tend to rotate and descend in response to intra-abdominal pressure.

Hypermobility can be the result of pregnancy or the ensuing childbirth or from other factors that tend to weaken the relevant muscles. In still further cases, urinary incontinence in women results from the combined effects of ISD and hypermobility. Even further still, a number of other conditions can contribute to urinary incontinence in women. For example, congenital defects, disease, injury, aging, and urinary tract infection can all lead to urinary incontinence. As one will appreciate, women suffering from incontinence unfortunately experience an involuntary escape of urine, particularly during coughing, sneezing, and other actions that produce an increase in intra-abdominal pressure.

Advantageously, it has been discovered that female stress incontinence can be corrected by surgical restoration of the urethrovesical junction to its proper orthotopic position. Stated alternatively, female urinary incontinence can be remedied by suspending, stabilizing, and/or compressing the bladder neck to achieve a position wherein incontinence will be avoided but normal urinary function will not be hindered. For the remedial procedure to be successful, the position of the bladder neck must be high enough to avoid incontinence even when under stress while not being so high that proper bladder voiding is prevented.

The prior art discloses a plurality of methods and devices for carrying out urethrovesical suspension procedures. For example, female urinary stress incontinence has been treated surgically by effectively tying the urethrovesical junction to the back of the symphysis pubis. Beginning at least as early as 1913 and extending to the present, a number of skilled inventors including Kelly, Lemay, Pereyra et al., Burch, Stamey, Mueller et al., and Cobb et al. together have defined the present state of the art and have helped to refine particularized apparatuses and techniques in the hope of yielding improved results.

For example, four relatively non-invasive surgical procedures for bladder neck suspension are described in Hadley et al., Urologic Clinics of North America, Vol. 12, No. 2, p. 291 (1985). In the original Pereyra method, a needle is passed from a suprapubic incision to an incision in the vagina near the bladder neck. Suture material is passed several times from the bladder neck to the suprapubic incision to suspend the bladder neck. The Cobb-Radge method inserts the needle from below through the vaginal incision. The Stamey procedure uses an endoscope to prevent the surgical needle from puncturing the bladder, and a Dacron vascular graft is used to anchor a nylon suture in the periurethral tissue. Under the Raz method, the surgeon inserts his or her finger through the vaginal incision to guide the suspension needle and avoid penetration of the bladder by the needle. The sutures are anchored by threading through tissue of the vaginal wall and tissue in the suprapubic area.

Unfortunately, many prior art techniques have involved cutaneous incisions and have commonly required that the patient be subjected to a general anesthesia. Furthermore, many such procedures are not conveniently subject to repeat applications notwithstanding the unfortunate reality that second and further operations can be necessary in many cases. Still further, a number of these procedures have been found to cause urethral distortion. Even further still, procedures involving suturing the urethral lumen directly to the symphysis pubis and placing additional sutures through the bladder have been found to result in urine loss and, possibly, the formation of bladder stones. Additionally, these relatively invasive methods can lead to other complications including enteropecele (a hernia within the vaginal wall) and genital prolapse, a descending of the uterus as a result of a weakness in the pelvic floor. Yet further, women undergoing such procedures can require six weeks or more before their preoperative lifestyle can be resumed.

In a relative advance in the art, U.S. Pat. No. 5,013,292 to Lemay discloses a method and kit for correcting female urinary incontinence wherein only a local anesthesia is required. The Lemay patent calls for the implantation of a head portion of an implant in the skin above the symphysis pubis. Ultimately, the head portion rests on the symphysis pubis with two dangling ends of a suture portion extending therefrom to allow an adjustment the urethrovesical angle. Unfortunately, as detailed below, even this improved Lemay device and procedure are quite complex and require a number of incisions to be made in a patient's abdominal skin. Not only do such incisions add to the discomfort associated with the procedure, but they also increase the risk of infection, dehiscence, and osseous complications.

Stated most basically, the Lemay procedure begins with the cutting of an approximately 1 cm incision in the vaginal mucosa at the urethrovesical junction, which is followed by the insertion of a hollow needle or cannula through the incision, through the space of the retzius, and outwardly through the patient's skin at a point where a 0.5 cm cutaneous incision is then made. A trocar is then removed from the need, and, while the cannula is still in place, one end of one suture of a first implant is slid through the cannula until the suture protrudes through the vagina. The needle is then removed, and, with the trocar again attached, the needle is reinserted at a different point in the vaginal incision until it passes through the cutaneous incision. The trocar is then removed, and the second end of the suture of the first implant is passed through the cannula to the vagina. Essentially the same procedure is performed relative to the second implant at a slightly displaced location. Then, the implants are buried under the skin overeat symphysis pubis, the urethrovesical angle is adjusted to a desired position, and the ends of the sutures are tied to act as a support to suspend, compress, and/or stabilize the urethrovesical junction at a desired angle.

U.S. Pat. No. 4,705,040 to Mueller et al., entitled Percutaneous Fixation of Hollow Organs, describes another method and device for supporting, compressing, and/or stabilizing a hollow body organ. Under the Mueller et al. method, a hollow needle carrying a T-shaped head with a trailing filament is driven through a patient's skin. The T-shaped head is then released from the needle, and the organ is fixed in a supported, compress, and/or stabilized position by an adjusting of the tension in the filament and a clamping of the filament outside the patient's body. Disadvantageously, the Mueller et al. method and device also requires for its installation that an incision be made in the patient's skin.

In light of the present state of the art as outlined above, a number of observations can be made. Most basically, it is clear that a number of proficient inventors have cooperated, both through individual and in collaborative efforts, to provide a progression of improved methods and devices for supporting, compressing, and/or stabilizing organs and, more particularly, for confronting female incontinence. It is also clear, however, that even those devices and procedures presently considered simplified and minimally invasive require rather complex surgical procedures and devices and call for the cutting of a number of incisions in a patient's skin and elsewhere. With this, even these improved methods and devices leave a patient at risk of infection, dehiscence, osseous, and still other complications.

Consequently, one considering the present state of the art will appreciate that there remains a need for a method and device for correcting female incontinence that eliminates the need for skin incisions, that is simple in construction and use, and that thereby remedies the numerous deficiencies left by the prior art.

SUMMARY OF THE INVENTION

Advantageously, the present invention is founded on the most basic object of providing an anchoring member with at least one trailing suture and a method and device for applying and adjusting those structures to support a bodily element of a patient, such as the urethrovesical junction in a female patient.

In particular embodiments, the invention provides a method and device for correcting incontinence, particularly female incontinence, that solves the problems that have hindered the prior art while demonstrating a plurality of further advantages thereover.

A fundamental object of the invention is to provide a method and device that can be employed, for example, to correct female incontinence in an effective manner while not hindering normal urinary function.

Another basic object of the invention is to provide such a device and method that does not require cutaneous incisions for its implantation.

A further object of the invention is to provide such a device, which may be employed for correcting female incontinence, that is simple in construction.

Yet another object of the invention is to provide a method, which can be used for correcting female incontinence, that can be carried out relatively simply, conveniently, and with minimal trauma to a patient.

An underlying object of the invention is to provide such a method and device that minimizes the risk of infection, dehiscence, and osseous complications resulting from the procedure.

These and further objects and advantages of the present invention will be readily obvious not only to one skilled in the art who has reviewed the present disclosure but also to patients and physicians who experience an embodiment of the present invention in installation and effect.

In accomplishing the aforementioned objects, a most basic embodiment of the present invention is exemplified by a method for the transvaginal correction of urinary incontinence in females without percutaneous incision. There, the method can begin with the steps of providing a delivery needle that comprises an elongate cannula with a proximal end and a distal end, providing a stylet that comprises an elongate rod for being matingly received into the cannula of the delivery needle, and providing a support, which can be termed a urethrovesical support, that comprises an anchor toggle with at least a first suture that has a proximal end fixed possibly to a central portion thereof.

With these elements provided, the distal end of the elongate cannula of the delivery needle is then inserted partially into the area of the patient's perineum, such as through the vagina of a female patient's body that has a bladder structure with a bladder, a urethrovesical junction, and a urethra. With a small incision made in the upper wall of the vagina or perineum and first and second lateral incisions made to opposite sides of, for example, the urethra, the distal end of the cannula is passed through the small incision, through the first or second incision, across the space of the Retzius behind the symphysis pubis, and then to a desired supporting location. Once the distal end of the cannula is in the desired supporting location, the anchor toggle of the urethrovesical support is deployed by sliding the elongate rod of the stylet increasingly deeper into the cannula of the delivery needle until the distal end of the elongate rod drives the anchor toggle out of the distal end of the cannula and into the desired supporting location.

With the anchor toggle so located, the elongate cannula of the delivery needle can be removed from the patient's body thereby leaving the anchor toggle in position and leaving the at least one elongate first suture in place tracing the path of the cannula of the delivery needle. Finally, the at least one suture can be supportingly coupled to, by way of example, the bladder structure of the patients body thereby providing support to the bladder structure with the anchor toggle acting as a supporting anchor and the at least one suture acting as a supporting line.

With certain embodiments of the present invention for a method and device generally described, relating in this case to a method and device for the transvaginal correction of urinary incontinence in females, one will appreciate that the foregoing discussion broadly outlines the more important features of the invention. As such, the foregoing is designed merely to enable a better understanding of the detailed description that follows and to instill a better appreciation of the inventor's contribution to the art. Before any particular embodiment of the invention is explained in detail, it must be made clear that the following details of construction, descriptions of geometry, and illustrations of inventive concepts are mere examples of the many possible manifestations of the invention.

DETAILED DESCRIPTION OF PREFERRED EMBODIMENTS

Figure 1:
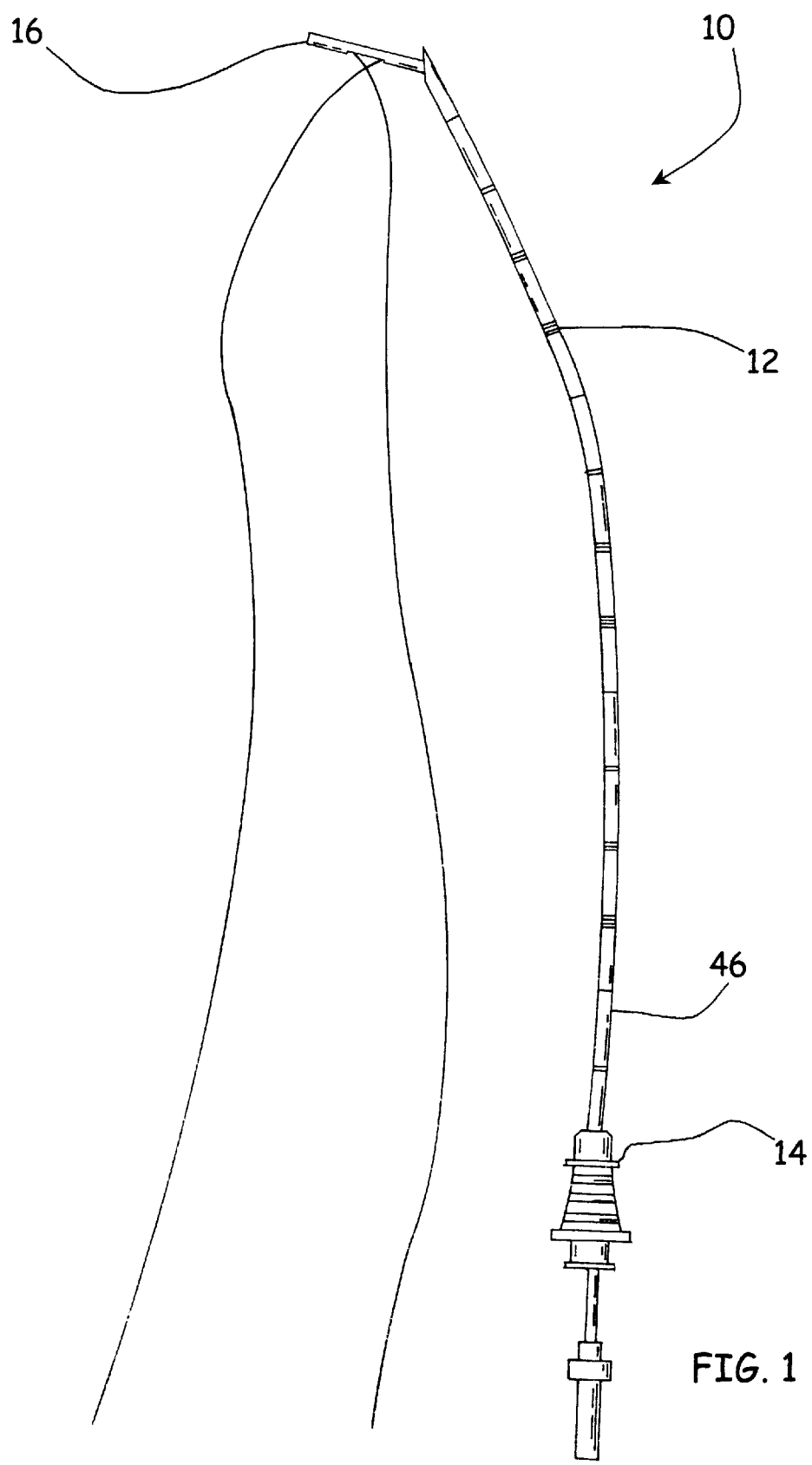
FIG. 1 is a perspective view of a device under the present invention with the anchor toggle of the support partially displaced from the slot in the trocar of the delivery needle.

As is the case with many inventions, the present invention for a method and device for supporting a bodily element is subject to a wide variety of embodiments. However, to ensure that one skilled in the art will be able to understand and, in appropriate cases, practice the present invention, certain preferred embodiments of the broader invention revealed herein are described below and shown in the accompanying drawing figures.

With this in mind and looking more particularly to the accompanying figures, an exemplary embodiment of the present invention for a device for supporting a bodily element is described below in the form of a device for the transvaginal correction of urinary incontinence. There, the device for the transvaginal correction of urinary incontinence is indicated generally at 10 in FIG. 1. One sees that the device for correcting urinary incontinence 10 is founded on three basic structures: a delivery needle 12, a stylet 14, and a urethrovesical support 16, the structure and use of each of which will be discussed in detail below. The device 10 can be effective in the suspension of bodily elements in both male and female patients. The device 10 is particularly useful for correcting urinary incontinence in females whether that incontinence is the result of intrinsic sphincter deficiency (ISD) wherein the urethral sphincter does not coapt properly, hypermobility wherein the structures adjacent to the bladder neck relax such that the bladder neck and proximal urethra tend to rotate and descend in response to intra-abdominal pressure, a combination of the two, or from any other of a plurality of potential sources.

Figure 2:
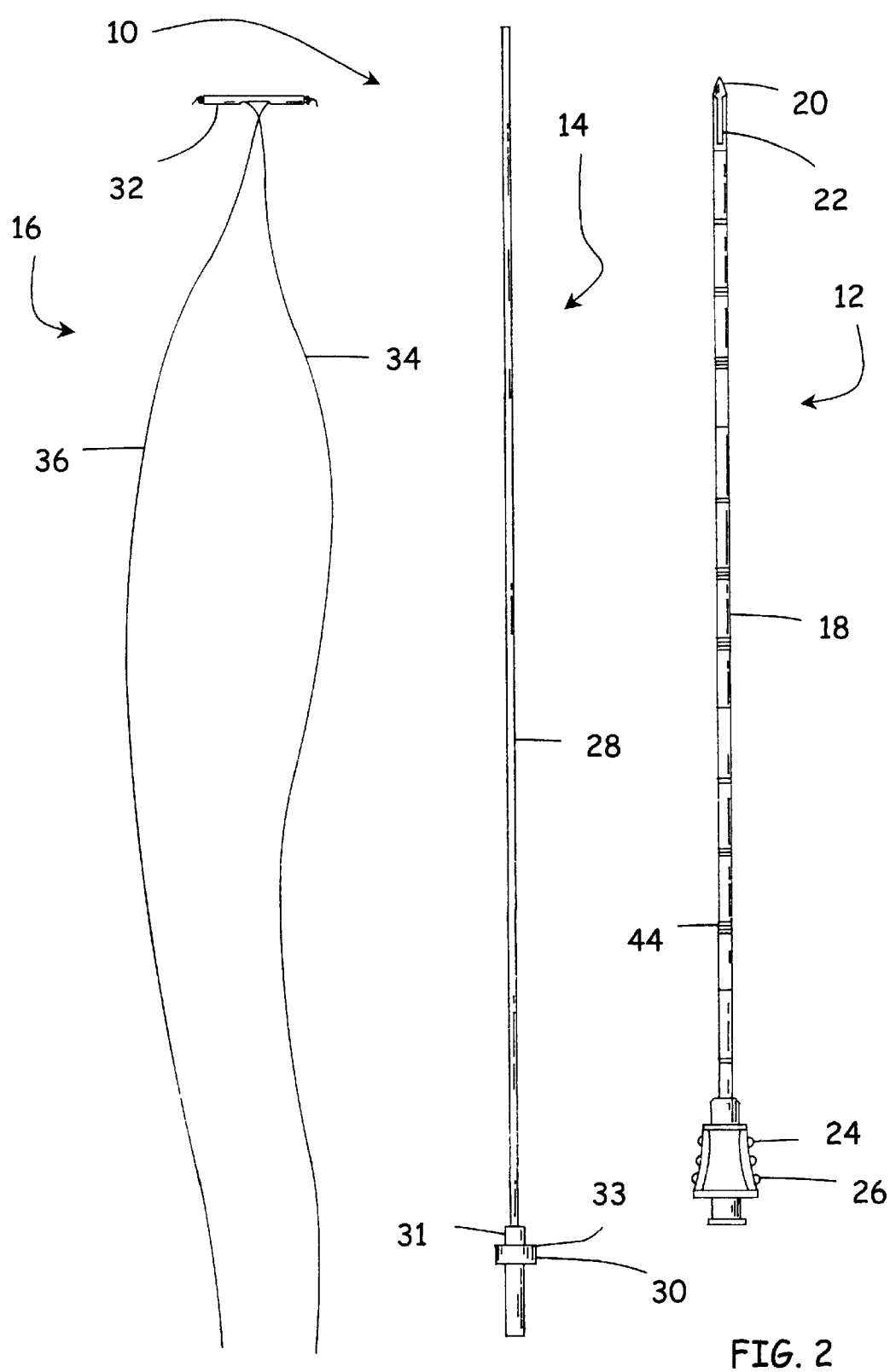
FIG. 2 is a view in front elevation of the support, the stylet, and the delivery needle of the embodiment of the device for use in the suspension of a bodily element such as in the transvaginal correction of urinary incontinence in females of FIG. 1.

By reference to FIG. 2, one sees that the delivery needle 12 comprises a cannula, or flexible tube, 18 that terminates at a trocar, or sharp point, 20 at a distal end thereof. Furthermore, the delivery needle 12 has an aligning handle 24 fixed to a proximal end thereof. In this case, the cannula 18 and the trocar 20 are formed from a single tube of material, which may preferably be metal. The proximal end of the cannula 18 is fixed to the aligning handle 24 as by being embedded therein. The trocar 20 is essentially formed by a cutting of the distal end of the cannula 18 at an angle such that the distal end comprises a sharp point, or trocar 20. A longitudinal slot 22 is formed in the cannula 18 beginning at a proximal end of the trocar 20 and terminating a short distance away at a given point along the length of the cannula 18.

As FIG. 1 shows most clearly, the distal portion of the cannula 18 has a curve therein. The longitudinal slot 22 and the proximal end of the trocar 20 are disposed on the inner side of the curve while the distal tip of the trocar 20 is disposed on the outer side of the curve. Where employed relative to a female patient for correcting urinary stress incontinence, the curve in the cannula 18 and the orientation of the trocar 20 relative thereto advantageously allow the delivery needle 12 to perform its function of traversing the space of the Retzius in the female patient while maintaining the sharp end of the trocar 20 close to the back of the pubic symphysis and away from the bladder, neither of which are shown in these early figures, and while preventing the trocar 20 from digging into or snagging on the pubic symphysis.

The aligning handle 24, which again is fixed to the proximal end of the cannula 18, enables a surgeon to control the delivery needle 12 during performance of the urinary stress incontinence correction procedure. Furthermore, the aligning handle 24 can assist the surgeon in appreciating the orientation of the cannula 18 and trocar 20 including during the urinary stress incontinence correction procedure wherein the cannula 18 and trocar 20 are for the most part beyond visual perception. This is accomplished by at least two means for providing an indication of the orientation of the delivery needle 12.

A first such means comprises a visual orientation marker 46 on a given side of the aligning handle 24. Of course, the visual orientation marker 46 could be disposed with substantially similar result to a first side of the curve, a second side of the curve, the inside of the curve, or the outside of the curve. In this case, the visual orientation marker 46 is disposed on the aligning handle 24 to the outside of the curve in the cannula 18. One may also appreciate that the visual orientation marker 46 could be created in a number of ways. In this case, it comprises an appropriately located color marking, which is also indicated at 46, that in this case comprises a blue stripe on the aligning handle 24.

The second means for providing an indication of the orientation of the delivery needle 18 comprises a tactile orientation indicator 26. Of course, the tactile orientation indicator 26 also could take a number of forms. In this case, it comprises a plurality of ridges, which are also indicated at 26, disposed on the aligning handle 24 to the first and second lateral sides of the curve in the cannula 18 but not to the inside and outside of the curve in the cannula 18.

Advantageously, the cannula 18 is further provided with a means for indicating the depth to which the cannula 18 has been inserted. As a result, especially in combination with the above-described means for providing an indication of the orientation of the delivery needle 18, a surgeon can gain a very good approximation of where the trocar 20 of the delivery needle 18 is at any given time. This, of course, can enable a safer, more accurate, and more efficient performance of the present procedure.

Although it is possible that the means for indicating the depth to which the cannula 18 has been inserted also could pursue a variety of forms, in this preferred embodiment it comprises a series of coded annular depth calibration stripes 44 disposed along the length of the cannula 18. The depth calibration stripes 44 comprise a sequence of 5 stripe designs each spaced 1 cm from one another. Beginning from the distal tip of the trocar 20 the stripes 44 begin with a narrow single stripe 44 indicating a 1 cm depth followed by narrow double stripes 44, narrow triple stripes 44, narrow quadruple stripes 44, and then a wide stripe 44 indicating 2 cm, 3 cm, 4 cm, and 5 cm depths respectively. That pattern continues along the length of the cannula 18 until the aligning handle 24 is reached. Of course, the stripes 44 could be differently spaced and sequenced and need not be spaced according to a metric scale.

Looking next to the stylet 14, one sees best in FIG. 2 that the stylet 14 is formed from an elongate deploying rod 28 with a free distal end and a deploying handle 30 fixed to a proximal end thereof. As FIG. 1 indicates, the deploying rod 28 is slidingly and matingly received through the aligning handle 24 and into and along the cannula 18. The deploying rod 28 preferably is formed from a malleable material such that it will be able to follow the curve in the cannula 18 of the delivery needle 12 without binding, crimping, or otherwise becoming obstructed within the cannula 18. In this embodiment, the stylet 14 is axially symmetrical in all respects. The deploying handle 30 of the stylet 14 has a neck 31 for being received into the aligning handle 24 and a shoulder 33 for positively engaging the most proximal end of the aligning handle 24.

For effectively deploying the support 16, which may in this embodiment be termed a urethrovesical support 16, as will be discussed further below, the preferred stylet 14 has a length from the distal surface of the shoulder 31 to the tip of the deploying rod 28 that is at least equal to the distance along the path of travel of the delivery needle 12 from the most proximal point on the aligning handle 24 to the proximal end of the trocar 20 at the distal tip of the cannula 18. In other words, the length of the stylet 14 from the distal surface of the shoulder 31 to the tip of the deploying rod 28 is preferably approximately at least as long as the straightened length of the delivery needle from the proximal end of the aligning handle 24 to the proximal end of the trocar 20.

The preferred cannula 18 has a length of approximately 8 inches from the distal surface of the aligning handle 24 to the most distal end of the trocar 20. Also, the cannula 18 preferably is formed from a 14 gage tube with an outside diameter of approximately 0.83 inches and an inside diameter of approximately 0.67 inches. The slot 22 preferably is approximately 0.025 inches wide and extends approximately 0.7 inches from the distal end of the trocar 20. The curve in the cannula 18 has a preferred radius of curvature of approximately 3.5 inches. Preferably, the bond between the cannula 18 and the aligning handle 24 will be able to withstand an axial pull force of at least 10 pounds. The deploying rod 28 is cut to a length of approximately 9.485 inches and has an outside diameter of approximately 0.035 inches. However, approximately 0.65 inches of the deploying rod 28 is retained within the deploying handle 30 whereby 8.85 inches of the deploying rod 28 extends from the deploying handle 30.

One skilled in the art will appreciate that the deploying rod 28 of the stylet 14 could be formed from a variety of materials. For example, the deploying rod 28 may preferably be formed from a variety of metallic or other materials provided they demonstrate the required flexibility for traversing the curve in the delivery needle 12. Of course, it is also important that the material be biocompatible. By way of example, the deploying rod 28 could be formed from resilient injection molded inert plastic or from stainless steel. In a preferred embodiment, the deploying rod 28 can be formed from a suitable memory metal, ideally a nickel titanium alloy, such as'that commercially available as Nitinol, which displays pseudoelasticity in at least the 15–45 degree Celsius temperature range.

Figure 5:
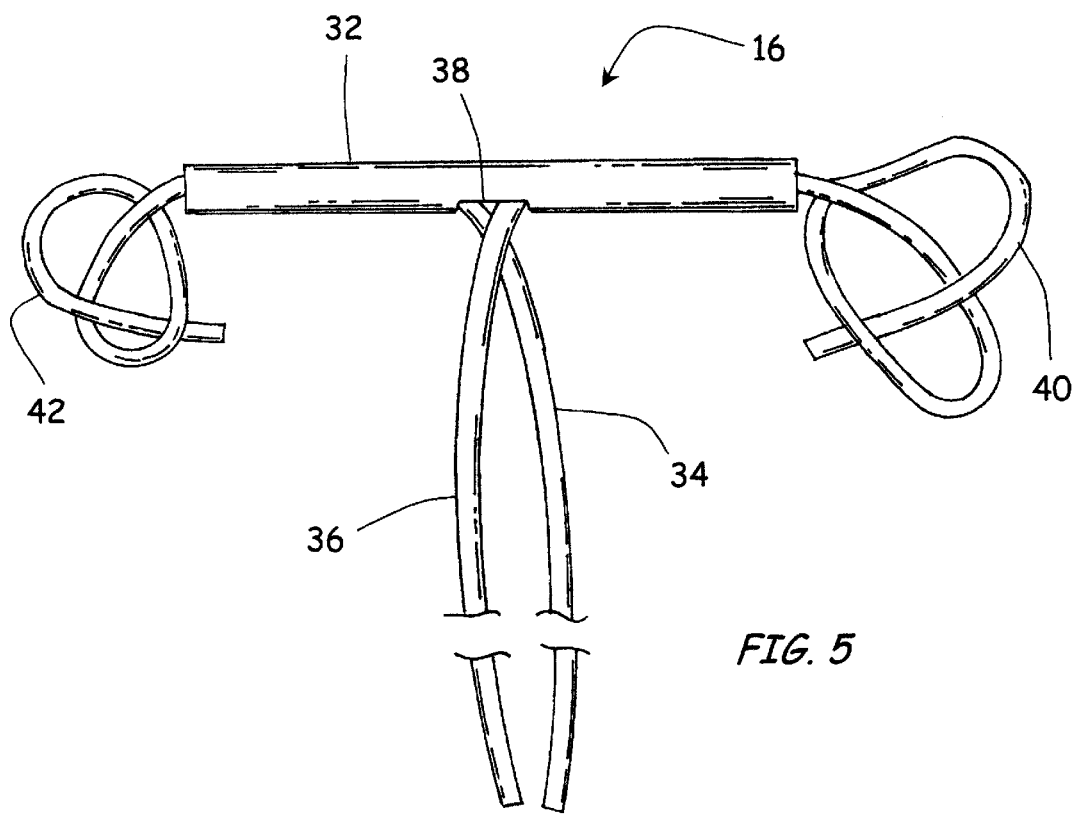
FIG. 5 is an enlarged view in front elevation of the support according to the present invention.

Looking next to the urethrovesical support 16, which also can be best seen in FIG. 2 and then in a larger view in FIG. 5, one sees that it is formed from an anchor toggle 32 that has first and second elongate sutures 34 and 36 trailing from a mid portion of the anchor toggle 32. The anchor toggle 32 comprises a relatively small cylinder, which in this embodiment is formed from a stainless steel alloy, such as 316L stainless steel. In the present embodiment, the anchor toggle 32 is approximately 0.5 to 0.75 inches in length and of a diameter appreciably less than the inner diameter of the cannula 18 of the delivery needle 12. More particularly, the presently preferred anchor toggle 32 is approximately 0.65 inches long with an outside diameter of approximately 0.062 inches and an inside diameter of approximately 0.034 inches.

As FIG. 5 illustrates most clearly, the first and second sutures 34 and 36 have proximal ends that enter the anchor toggle 32 through a central aperture 38 in the cylindrical anchor toggle 32. The preferred central aperture 38 comprises an approximately 0.125 inch long slot in a mid-portion of the anchor toggle 32 that has rounded edges to prevent damage to the first and second sutures 34 and 36. The proximal ends of the first and second sutures 34 and 36 are fixed relative to the anchor toggle 32 by first and second knots 40 and 42. To do so, the proximal ends of the sutures 34 and 36 are first slid through the central aperture 38 and out opposite ends of the anchor toggle 32. Then, the first and second knots 40 and 42 are tied, and the first and second sutures 34 and 36 are pulled taut. With this, the first and second sutures 34 and 36 may naturally tend to cross over one another as FIG. 5 depicts.

One skilled in the art will appreciate, of course, that the first and second sutures 34 and 36 could be formed from a variety of filamentary materials including, for example, polypropylene. Likewise, the thickness of the first and second sutures 34 and 36 can vary within the scope of the invention. At present, the first and second sutures 34 and 36 are most preferably formed from #1 blue mono polypropylene. Even further, it must be appreciated that, although the first and second sutures 34 and 36 are shown as separate structures herein, it is well within the scope of the invention to form the first and second sutures 34 and 36 from a single length of suture material with trailing opposite ends comprising the first and second sutures 34 and 36. Further still, one will appreciate that the length of the first and second sutures 34 and 36 can be varied to suit particular patients and other factors. Preferably, the first and second sutures 34 and 36 have approximate lengths from their distal ends to the point where they enter the central aperture 38 of approximately 14 inches.

Figure 3:
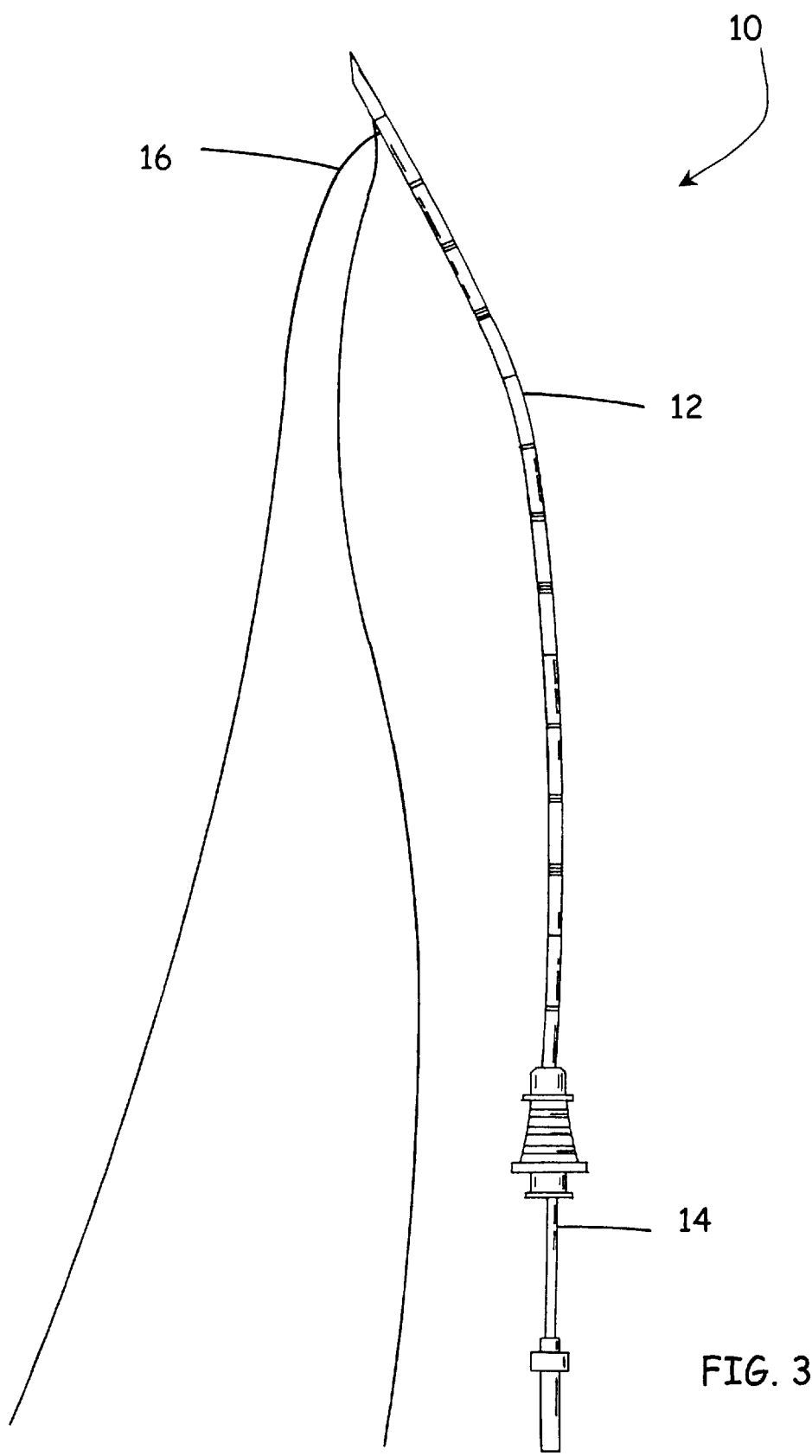
FIG. 3 is a view in side elevation of the device for use in the suspension of a bodily element such as in the transvaginal correction of urinary incontinence in females with the anchor toggle of the support fully retained in the slot in the trocar of the delivery needle.

Under this arrangement, the device 10, which can be used for the transvaginal correction of urinary incontinence in females 10, allows for the remote deployment of the anchor toggle 32 of the urethrovesical support 16 from the distal end of the delivery needle 12. To do so, the deploying rod 28 of the stylet 14 is first slightly withdrawn from the cannula 18 and the delivery needle 12 in general. The anchor toggle 32 is then inserted through the trocar 20 and into the cannula 18 of the delivery needle 12 with the first and second sutures 34 and 36 aligned with the slot 22 whereby the first and second sutures 34 and 36 are received into the slot 22. The anchor toggle 32 can then be slid into the cannula 18 until the first and second sutures 34 and 36 contact the proximal end of the slot 22 as is shown in FIG. 3.

With this, the trocar 16 can be used to pierce a given interior or exterior body surface and the delivery needle 12 can be slidingly guided into the body with the first and second sutures 34 and 36 trailing alongside the outside of the length of the cannula 18 and with the distal ends of the first and second sutures 34 and 36 remaining outside of the entry point of the delivery needle 12. Once the distal end of the delivery needle 12 is in the position where it is desired to deploy the anchor toggle 32 (as indicated by the orientation means 26 and 46, the depth calibration markers 44, and the surgeon's senses and expertise), the deploying rod 28 of the stylet 14 can be slid deeper into the delivery needle 12.

As a result, the distal end of the deploying rod 28 will contact the anchor toggle 32 and drive it out of the cannula 18 and trocar 20 thereby remotely deploying it. The delivery needle 12 can then be withdrawn from the patient's body thereby leaving the anchor toggle 32 and the first and second sutures 34 and 36 in place. The support 16 can then be completely formed by tying the distal ends of the first and second sutures 34 and 36 in place in support of a given body part with the anchor toggle 32 providing the requisite anchoring support, stabilization, and/or slight compression for the body part.

Of course, one skilled in the art will be aware that the above-described support 16 could be used to great advantage in a number of procedures. However, the present invention has been found particularly advantageous for carrying out the correction of urinary stress incontinence by implantation through the perineum of a patient. With this, the device 10 can be used to great advantage in the transvaginal correction of urinary stress incontinence in females. Advantageously and in a marked deviation from the prior art, the present inventor has devised of an installation procedure that requires no cutaneous incisions. A greater understanding of this procedure can be gained be in FIGS. 4 through 4G where various stages and refinements of a procedure for correcting urinary stress incontinence in a female patient are shown with it being expressly noted that the present invention could be used to equal advantage relative to male patients and in other procedures.

Figure 4:
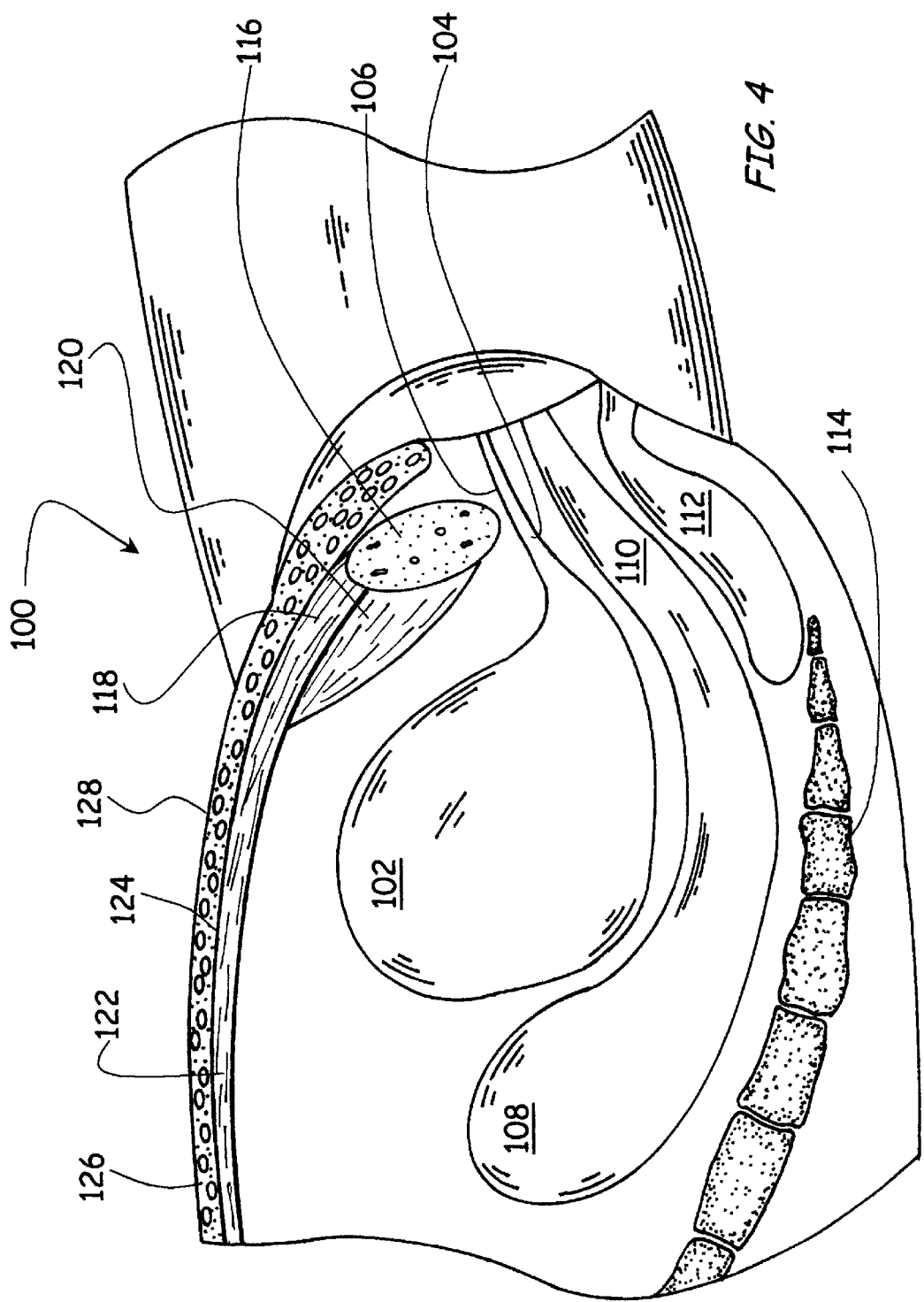
FIG. 4 is a longitudinal cross section taken through the pelvic region of a female patient.

In FIG. 4, a simplified cross section of a female patient's body is indicated generally at 100. There, one sees that the bladder 106 meets the urethra 106, or bladder neck 106, at a urethrovesical junction 104. Adjacent to the bladder 102 is the uterus 108, which leads to the vagina 110. The rectum 112 lies below the urethra 106 and the vagina 110, and the coccyx 114 progresses from below the rectum 112. Above the urethra 106 is the symphysis pubis 116, or pubic bone 116, to which is coupled to Cooper's or pectineal ligament 118 and the pyramidalys 120. The rectus abdominus, or abdominal muscle 122, which is contained in a sheath of the rectus 124, progresses along away from the symphysis pubis 116. Disposed over the rectus abdominus 122 and adjacent structures is a layer of subcutaneous fat 126, which of course is covered by a layer of skin 128. For purposes of the present discussion, one can assume that the patient is suffering from urinary stress incontinence such that the urethrovesical junction 104 is in need of support, stabilization, and/or slight compression to eliminate unwanted loss of urine particularly during coughing, laughing, and increases in intra-abdominal pressure.

Figure 4A:
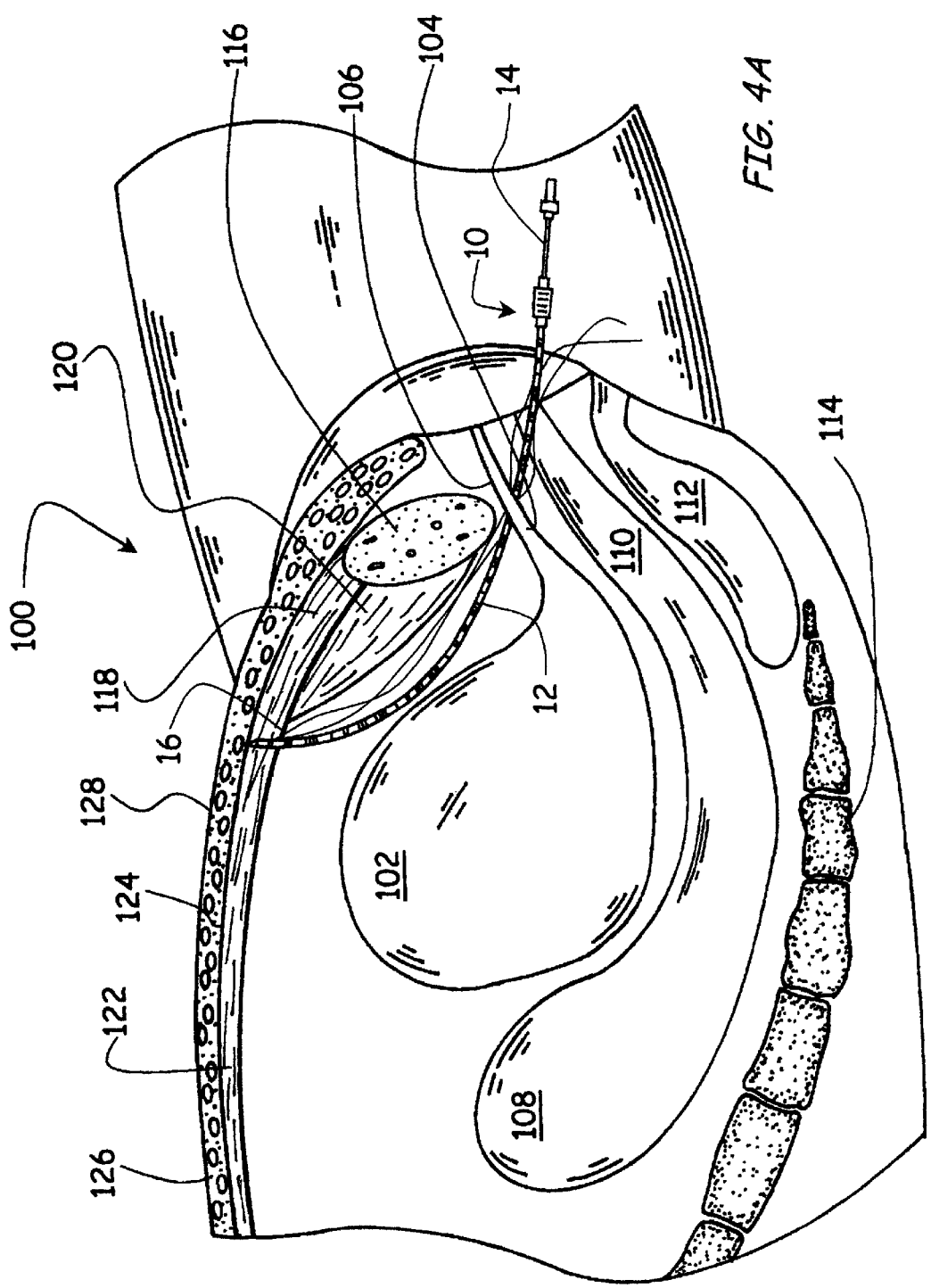
FIG. 4A is the cross section of FIG. 4 with the device for the suspension of a bodily element such as for the transvaginal correction of urinary incontinence in females in place prior to the deploying of the anchor toggle from the delivery needle.

Looking then to FIG. 4A, one sees the present invention for a process for the transvaginal correction of urinary stress incontinence in females depicted at an early stage. There, the anchor toggle 32 is shown installed in the distal end of the delivery needle 12 with the first and second sutures 34 and 36 received within and projecting from the slot 22 in the delivery needle 12 and trailing alongside the cannula 18 of the delivery needle 12.

Considering FIG. 4A in conjunction with FIG. 4E, one can perceive that a small incision 109 has been made in the upper vaginal wall 107 directly beneath the urethra 106, preferably below the urethrovesical junction 104. Also, with the access provided by the small incision 109 in the upper vaginal wall, a first lateral incision 111 has been made through the periurethral tissue 115 to a first side of the urethra 106, and a second lateral incision 113 has been made through the periurethral tissue 115 to a second side of the urethra 106.

With this, the distal end of the delivery needle 12 has been inserted partially into the vagina 110, and the trocar 20 of the delivery needle 12 has been guided into and through the incision 109 in the upper wall of the vagina 110. The distal end of the delivery needle 12 has then been guided upwardly through the first lateral incision 111 to the first side of the urethra 106 and through the space of the Retzius immediately behind the symphysis pubis 116 until the trocar 20 has pierced the rectus abdominus 122 thereby carrying the anchor toggle 32 therethrough. Of course, the distal end of the delivery needle 12 could just as well have been passed through the second lateral incision 113. In any event, with the delivery needle 12 so positioned, the first and second sutures 34 and 36 are left trailing alongside the delivery needle 12, through the first lateral incision 111, and through the small the incision 109 in the upper wall 107 of the vagina 110. As one will appreciate, achieving the aforedescribed location of the delivery needle 12 and the device for correcting urinary stress incontinence 10 in general would be done by a surgeon's combined reliance on the orientation markers 26 and 46, the depth calibration markers 44, and the surgeon's own experience, expertise, and knowledge of the patient's body 100.

Figure 4B:
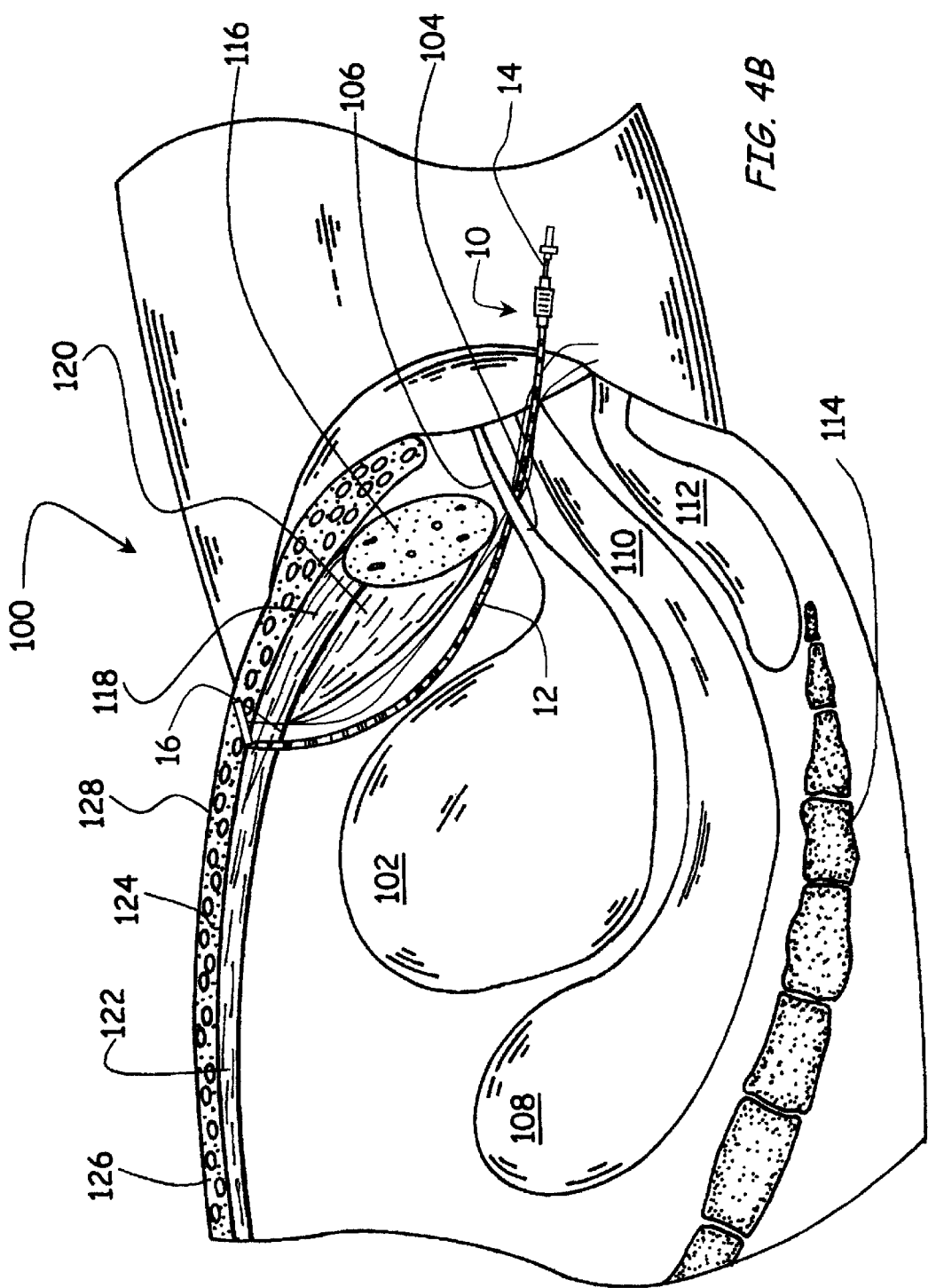
FIG. 4B is the cross section of FIG. 4 with the device for the suspension of a bodily element such as for the transvaginal correction of urinary incontinence in females in place with the anchor toggle deployed from the delivery needle.

With the device for correcting urinary stress incontinence 10 so situated, the anchor toggle 32 is in a proper position for being deployed so that it will remain above the rectus abdominus 122, Cooper's ligament 118, and the Pyramidalys 120 but below the skin 128 without need for percutaneous incision or piercing. FIG. 4B shows the anchor toggle 32 as it is being deployed from the delivery needle 12. To do so, the surgeon will grip and restrain the aligning handle 24 and then push the stylet 14 deeper into the delivery needle 12. With this, the distal tip of the deploying rod 28 will contact the proximal end of the anchor toggle 32 thereby driving the anchor toggle 32 and the first and second sutures 34 and 36 from their positions within the delivery needle 12. Once so dislodged from the delivery needle 12, the anchor toggle 32 will be securely in place to provide support to what is in this case the urethrovesical junction 104 but could comprise any of a plurality of organs by supporting the proximal ends of the first and second sutures 34 and 36 above the rectus abdominus 122, Cooper's ligament 118, and the Pyramidalys 120 or a number of other muscles or ligaments while leaving the first and second sutures 34 and 36 dangling therebelow.

Figure 4C:
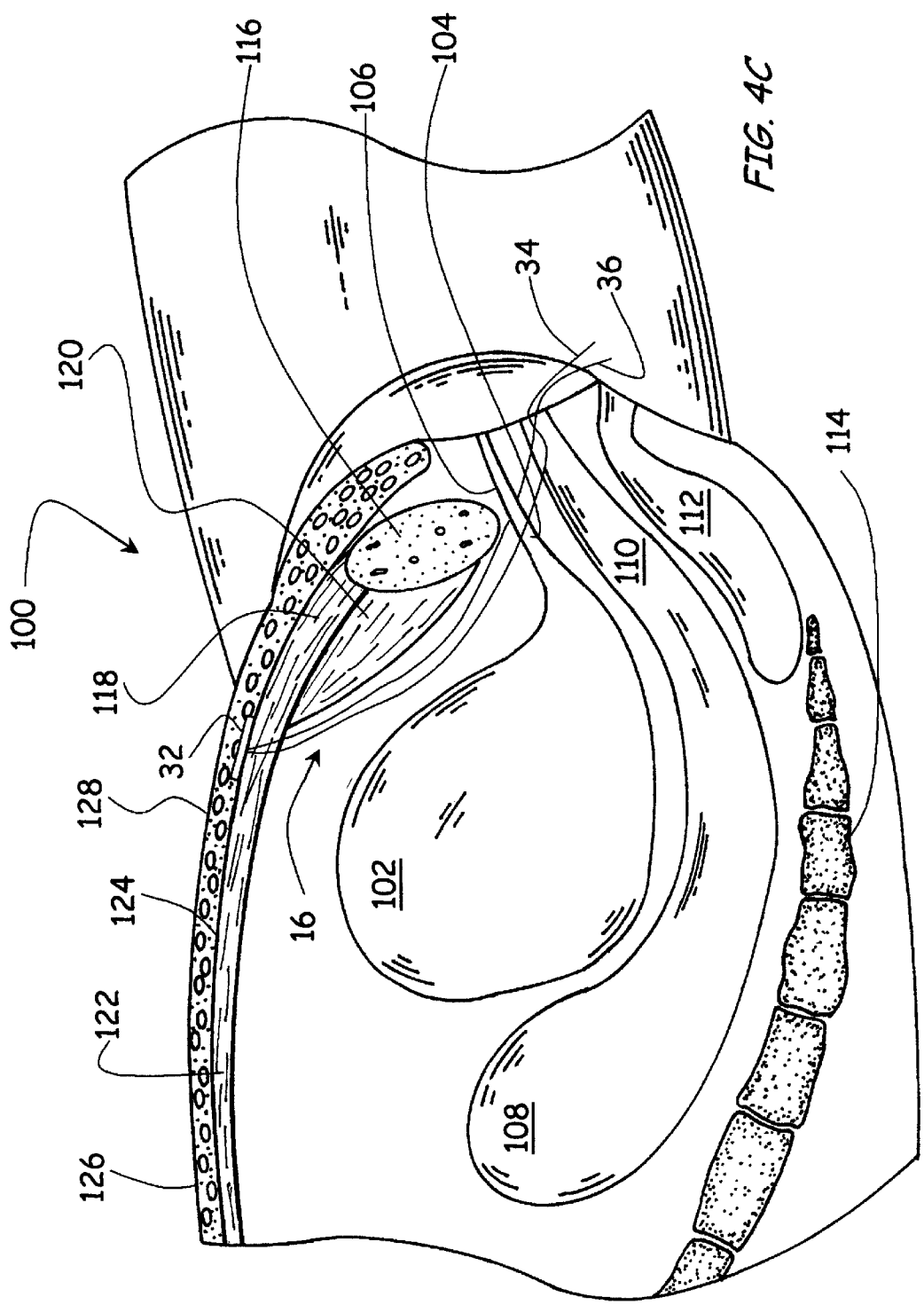
FIG. 4C is the cross section of FIG. 4 with the device for the suspension of a bodily element such as for the transvaginal correction of urinary incontinence in place with the anchor toggle fully deployed and the delivery needle removed.

With the anchor toggle 32 deployed, the surgeon can withdraw the delivery needle 12 from the patient's body 100 thereby leaving the urethrovesical support 16 disposed generally as is shown in FIG. 4C. However, the astute observer will appreciate in FIG. 4C that the first and second sutures 34 and 36 are disposed to opposite sides of the urethra 106, which was not the case initially since both passed through the first lateral incision 111. To accomplish this, the surgeon would manually pass the trailing end of the second suture 36 upwardly through the first lateral incision 111, over the urethra 106, and downwardly through the second lateral incision 113. As a result, the anchor toggle 32 maintains its position above the rectus abdominus 122, Coopers ligament 118, and the Pyramidalys 120 while the first and second sutures 34 and 36 extend from the anchor toggle 32, through the rectus abdominus 122, through Cooper's ligament 118, through the Pyramidalys 120 as necessary, through the space of the Retzius immediately behind the symphysis pubis 116, and then through the first and second lateral incisions 111 and 113 respectively into the common area adjacent to the small incision 109.

Figure 4D:
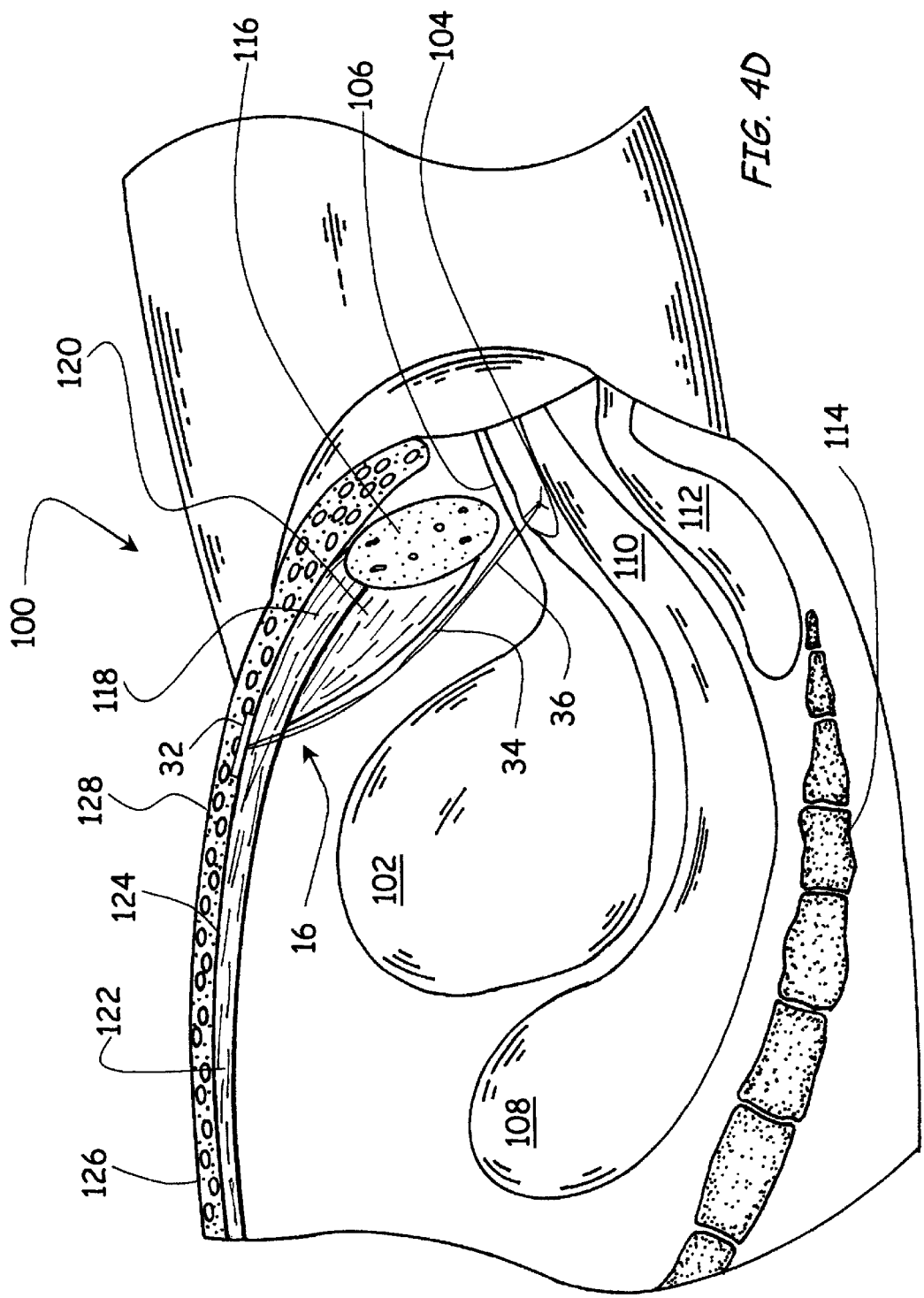
FIG. 4D is the cross section of FIG. 4 with the device for the suspension of a bodily element such as for the transvaginal correction of urinary incontinence in females in place with the first and second sutures tied in support, stabilization, and/or partial compression of the urethrovesical junction thereby in correction of urinary incontinence in the female patient.
Figure 4E:
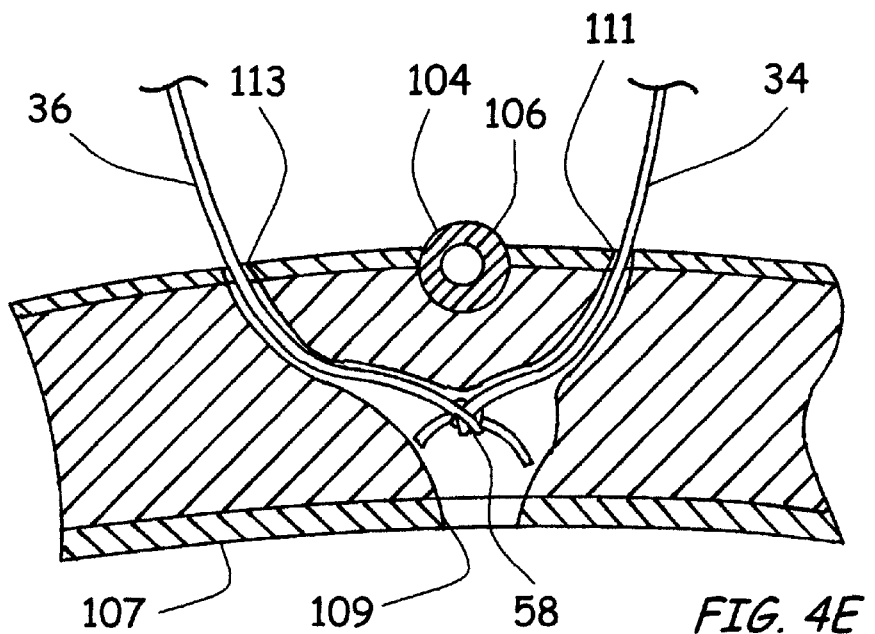
FIG. 4E is a lateral cross section taken through the pelvic region of a female patient with the device for the suspension of a bodily element such as for the transvaginal correction of urinary incontinence in females in place with the first and second sutures tied in support, stabilization, and/or partial compression of the urethrovesical junction thereby in correction of urinary incontinence in the female patient.

To complete this first procedural embodiment of the invention, the distal ends of the first and second sutures 34 and 36 are tied or otherwise secured in relation to one another below the urethra 106 as is shown in FIGS. 4D and 4E. Preferably, the ends of the first and second sutures 34 and 36 are so joined under the urethrovesical junction 104. With this, the urethrovesical support 16, which comprises the anchor toggle 32 in combination with the first and second sutures 34 and 36, will tend to support, stabilize, and/or slightly compress the urethra 106 and thereby to prevent urinary incontinence. Stated alternatively, the urethrovesical support 16 operates to restore or maintain the urethrovesical junction 104 in its correct anatomical position by providing a stable floor that counteracts internal stresses.

Of course, the surgeon must form the urethrovesical support 16 with sufficient tension to support, stabilize, and/or partially compress the urethra 106 sufficiently to avoid incontinence but not so much tension as to prevent normal urinary function or to cause bladder instability. This, of course, would be accomplished by an exercise of the surgeon's skill and discretion. Advantageously, under the present invention, the height at which the urethrovesical junction 104 is retained can be adjusted if and when necessary by a retying of the first and second sutures 34 and 36 either to raise the urethrovesical junction 104 if urinary incontinence re-manifests itself or has not been fully corrected or to lower the urethrovesical junction 104 if normal urinary function has been hindered. Of course, once the first and second sutures 34 and 36 are tied in their final positions, the distal ends of the first and second sutures 34 and 36 can be trimmed as necessary to prevent discomfort and other complications.

The abovedescribed method and device for correcting urinary incontinence 10 certainly would be effective in accomplishing the present invention's fundamental goal of correcting urinary incontinence in females. However, it should be noted that it may be preferable in certain instances to include further a sling or other structure for spreading the supporting force of the first and second sutures 34 and 36 over a greater surface area. A number of sling structures and materials undoubtedly would occur to one skilled in the art.

Figure 6:
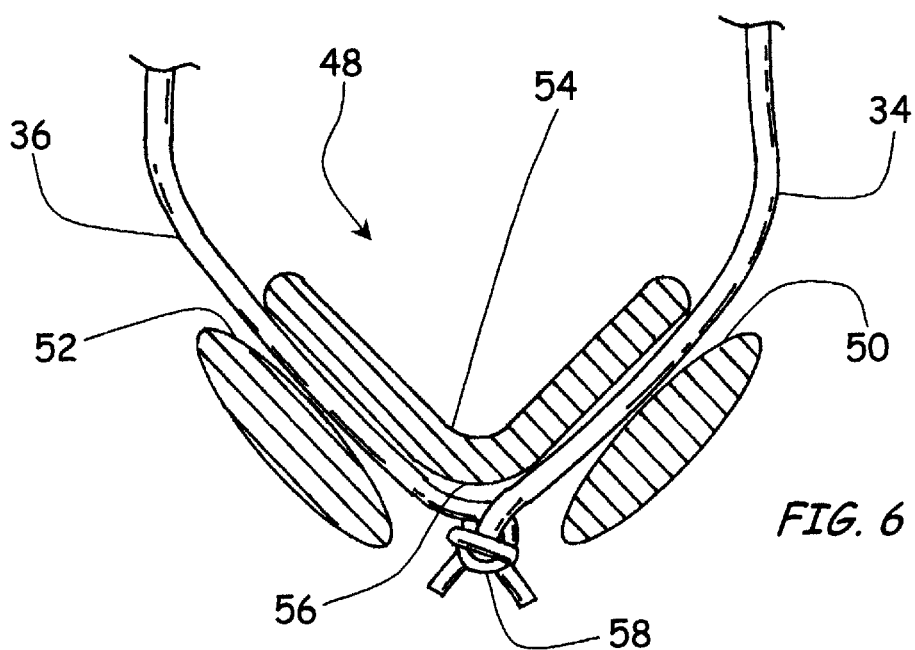
FIG. 6 is a cross sectional view of a junction support sling according to the present invention.

One possible support sling is indicated generally at 48 in the cross sectional view of FIG. 6. There, one sees that the sling 48, which in this procedure may be termed a urethrovesical junction support sling 48, has first and second receiving tubes 50 and 52 for receiving the first and second sutures 34 and 36. The first and second receiving tubes 50 and 52 lead to a tying junction 56 where the first and second sutures 34 and 36 can be tied in a knot 58. Most essentially, of course, the sling 48 has a smoothly shaped support portion 54 for cradling the urethra and particularly the urethrovesical support junction 104. With this, the urethra 106 and particularly the urethrovesical support junction 104 can enjoy smooth, comfortable support.

Figure 4F:
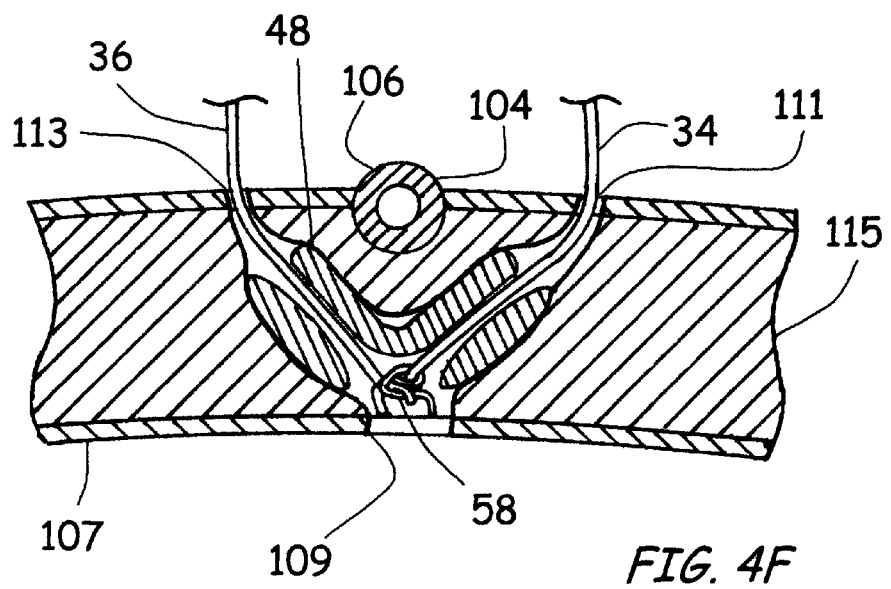
FIG. 4F is a lateral cross section taken through the pelvic region of a female patient with the device for the suspension of a bodily element such as for the transvaginal correction of urinary incontinence in females in place with the first and second sutures tied to the urethrovesical junction support sling of FIG. 6 in cooperative support, stabilization, and/or partial compression of the urethrovesical support junction.
Figure 4G:
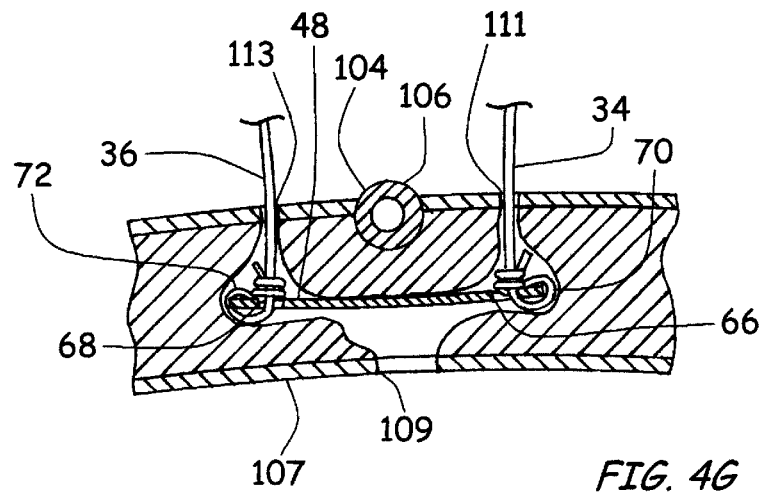
FIG. 4G is a lateral cross section taken through the pelvic region of a female patient with the device for the suspension of a bodily element such as for the transvaginal correction of urinary incontinence in females in place with the first and second sutures tied to the alternative urethrovesical junction support sling of FIG. 7 in cooperative support, stabilization, and/or partial compression of the urethrovesical support junction.

The urethrovesical junction support sling 48 of FIG. 6 is shown in place in the lateral cross-sectional depiction of FIG. 4F. To install the support sling 48 as shown in FIG. 6, the procedure would be carried out substantially as described previously except that the distal ends of the first and second sutures 34 and 36 would not yet be tied or otherwise coupled to one another. Then, the surgeon would pass the urethrovesical junction support sling 48 through the small incision 109 and then align it as is shown in FIG. 6 directly under the urethra 106 and preferably directly under the urethrovesical junction 104. If necessary, the surgeon could blunt the periurethral tissue 115 adjacent to the small incision 109 and the first and second lateral incisions 111 and 113 to accommodate the urethrovesical junction support sling 48. Prior, during, or after the urethrovesical junction support sling's 48 location within the periurethral tissue 115, the first and second sutures 34 and 36 must be respectively passed through the first and second receiving tubes 50 and 52 such that their ends enter the tying junction 56. With this, the ends of the first and second sutures 34 and 36 can be tied at a proper tension to ensure appropriate support for the urethrovesical junction 104.

Figure 7:
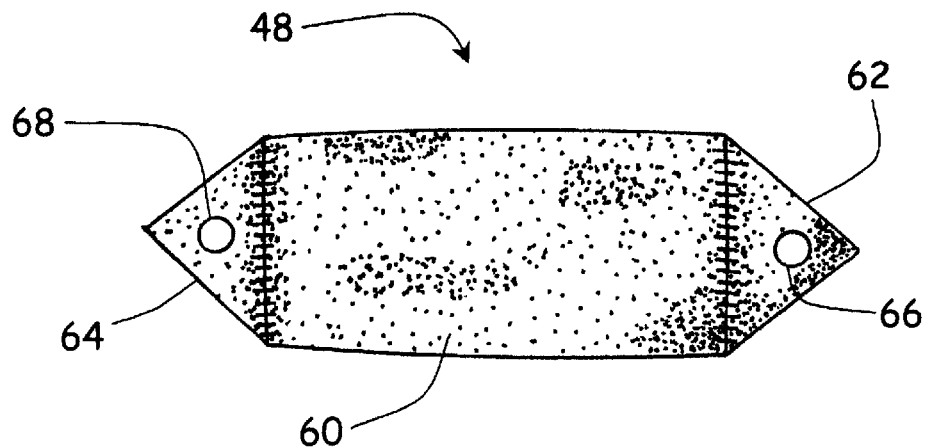
FIG. 7 is a top plan view of an alternative junction support sling according to the present invention.

FIG. 7 shows an alternative urethrovesical junction support sling 48. There, the support sling 48 is founded on a panel 60 of flexible material. The panel 60 has a first end 62 and a second end 64. In this representative embodiment, the first and second ends 62 and 64 are pointed, but this certainly need not be the case as they could be straight, rounded, or substantially any other shape. A first aperture 66 is disposed adjacent to the first end 62 of the panel 60, and a second aperture 68 is disposed adjacent to the second end 64 of the panel 60.

Installation of this alternative urethrovesical junction support sling 48 would be carried out substantially as with the first embodiment of FIGS. 6 and 4F with respect to getting the urethrovesical junction support sling 48 in place and ready for attachment. However, instead of tying the ends of the first and second sutures 34 and 36 together as in previous embodiments (although doing so is still possible), the urethrovesical junction support sling 48 is secured in place by tying or otherwise coupling the distal end of the first suture 34 to the first end 62 of the urethrovesical junction support sling 48 as with a knot 70 through the first aperture 66 and by tying or otherwise coupling the distal end of the second suture 36 to the second end 64 of the urethrovesical junction support sling 48 as with a knot 72 through the second aperture 68. Again, the first and second sutures 34 and 36 should be tied such that they provide sufficient support, stability, and/or slight compression to the urethra 106 to prevent urinary incontinence while not inhibiting normal urinary function.

The sling 48 could be made from a wide variety of synthetic and non-synthetic materials. Of course, the material employed for the sling 48 preferably should be biocompatible. The material could be filamentous. For example, the sling 48 could be crafted from filamentous non-synthetic materials including cadaveric or animal tissue such as fascia lata, rectus fascia, or processed collagen. Synthetic materials for the sling 48 include polyester, polyurethane, and nylon. Such materials could be woven or non-woven. The filaments of such materials could be braided together to form strands or threads that then can be braided or woven together thereby forming strips of fabric. The material for the sling 48 also could be non-filamentous. For example, the sling 48 could be crafted from silicone, polytetrafluoroethylene (PTFE), polyethylene terephthalate (PET), fluorinated ethylene propylene (FEP), or even thin films such as latex.

A number of even further factors can influence the material selection for the sling 48. For example, the material for the sling 48 could be chosen to achieve elasticity if that is desired. To do so, the sling 48 could be crafted from, by way of example, knitted polyester. Where a surgeon seeks to create an immobile floor, a minimally elastic material could be used such as, for example, woven polyester. Furthermore, material for the sling 48 could be chosen to be porous, microporous, perforated, or impermeable. Impermeable materials include nylon and polyester. Even further still, the sling 48 could be impregnated with antibiotics or other agents.

The material for the sling 48 could be directionally oriented or multidirectional. Suitable directionally oriented materials include natural materials such as grained or striated tissue. The tissue could be chosen, for example, from an allograft, a xenograft, or an autologous tissue. Where autologous tissue is employed, it is advantageously possible that it could revascularize and regrow after implantation. Autologous and allograft tissues can be procured from striated muscle, fascia lata, rectus fascia, dura, pericardium, and the vaginal wall. The allograft tissue can be obtained from a cadaver. Xenograft tissue can be retrieved from striated muscle, bovine fascia, dura, pericardium, and collagen. Of course, the foregoing materials are merely representative of the many possible materials that would readily occur to one skilled in the art and that are well within the scope of the present invention. For example, a variety of commercially available, synthetic, directionally-oriented materials could be employed including woven and knitted polyester.

It will also be readily appreciated that the size of the sling 48 can be varied significantly within the scope of the invention. The particular size will depend, of course, on a plurality of factors including the surgeon's preferences and practices and the particular patient whose incontinence is sought to be corrected. By way of example, the sling 48 of FIG. 7 could have a length of between about 2 and about 10 cm and a width of between about 1 and about 5 cm. Of course, these dimensions are merely representative and do not limit the scope of the present invention. It is entirely possible and it is entirely within the scope of the present invention that a given sling 48 may be well outside the above-specified representative ranges.

From the foregoing, one will appreciate that the present invention achieves a number of advantages over the prior art. Most fundamentally, by proper installation and, if necessary, adjustment of the urethrovesical support 16, the device for the transvaginal correction or urinary stress incontinence in females 10 can be implanted to correct urinary stress incontinence while not hindering normal urinary function. Advantageously, this can be accomplished under the present invention without need for cutaneous incision to the patient's abdomen or elsewhere whereby the risk of infection, dehiscence, and osseous complications is reduced. Even further, with the combined advantages deriving from the delivery needle 12, the stylet 14, and the urethrovesical support 16, the device for correcting urinary stress incontinence is not only simple in construction, but it is also capable of being installed relatively quickly, conveniently, and with minimal trauma to a patient. Naturally, one skilled in the art will be aware of still further advantages of the present invention in light of this disclosure.

It will be clear that the present invention has been shown and described with reference to certain preferred embodiments that merely exemplify the broader invention revealed herein. Certainly those skilled in the art can conceive of alternative embodiments. For instance, those with the major features of the invention in mind could craft embodiments that incorporate those major features while not incorporating all of the features included in the preferred embodiments. With the foregoing in mind, the following claims are intended to define the scope of protection to be afforded the inventor. The claims shall be deemed to include equivalent constructions insofar as they do not depart from the spirit and scope of the invention.

It must be further noted that a plurality of the following claims express certain elements as means for performing a specific function, at times without the recital of structure or material. As the law demands, these claims shall be construed to cover not only the corresponding structure and material expressly described in this specification but also equivalents thereof.

I claim as deserving the protection of United States Letters Patent:

1. A device for suspending, stabilizing, and/or slightly compressing a bodily structure, the device comprising:
   a delivery needle comprising an elongate cannula with a proximal end, a distal end, and a body portion;
   a stylet comprising an elongate rod for being matingly received into the cannula of the delivery needle; and
   a support comprising an anchor toggle and elongate first and second sutures wherein each of the first and second sutures has a first end secured to the anchor toggle and a free second end wherein each of the first and second sutures extend from a central portion of the anchor toggle;
   whereby the delivery needle and the stylet can be used to deploy the anchor toggle remotely in a desired location in a body to provide support for the first and second sutures and thereby to support, stabilize, and/or compress a bodily structure.

2. The device of claim 1 further comprising a trocar disposed at the distal end of the delivery needle.

3. The device of claim 1 further comprising a longitudinal slot formed in the delivery needle wherein the longitudinal slot begins at the distal end of the cannula, communicates longitudinally along the cannula, and terminates a given distance away from the distal end of the cannula whereby the support can be retained within the distal end of the delivery needle with the anchor toggle at least partially disposed in the distal end of the delivery needle and the first and second sutures protruding from the slot.

4. The device of claim 3 wherein the body portion of the delivery needle has a curve therein and wherein the slot is disposed on an inside of the curve whereby the first and second sutures protrude through the slot on the inside of the curve.

5. The device of claim 4 further comprising a trocar disposed at the distal end of the delivery needle wherein the trocar is angled such that the trocar has a distal tip and a proximal base and wherein the slot is disposed adjacent to the base of the trocar.

6. The device of claim 5 wherein the distal tip of the trocar is disposed on an outside of the curve in the delivery needle.

7. The device of claim 1 wherein the body portion of the delivery needle has a curve therein and further comprising an aligning handle fixed adjacent to the proximal end of the delivery needle.

8. The device of claim 7 further comprising a visual orientation marker on the aligning handle for indicating an orientation of the delivery needle wherein the visual orientation marker comprises a color marking disposed to a first side of the curve in the delivery needle but not to a second side of the curve in the delivery needle.

9. The device of claim 7 further comprising a tactile orientation indicator disposed on the aligning handle for indicating an orientation of the delivery needle.

10. The device of claim 9 wherein the tactile orientation indicator comprises a plurality of ridges disposed on the aligning handle wherein the plurality of ridges are disposed to a first side of the curve in the delivery needle but not to a second side of the curve in the delivery needle.

11. The device of claim 1 further comprising a means for indicating a depth to which the delivery needle has been inserted into a patient's body.

12. The device of claim 11 wherein the means for indicating the depth to which the delivery needle has been inserted comprises a series of depth calibration markings disposed along the body portion of the delivery needle.

13. The device of claim 12 wherein the series of depth calibration markings comprise a plurality of coded stripes wherein different numbers of stripes indicate different depths.

14. The device of claim 1 wherein the elongate rod of the stylet is formed from a nickel titanium alloy.

15. The device of claim 1 wherein the anchor toggle comprises a cylinder with an aperture in a central portion thereof and wherein the first and second sutures extend from the aperture in the central portion of the anchor toggle.

16. The device of claim 15 wherein the first and second sutures travel through the anchor toggle and out opposite ends thereof and wherein the first ends of the first and second sutures are secured to the anchor toggle by a knot in each suture tied beyond the opposite ends of the anchor toggle.

17. The device of claim 1 further comprising a sling for coupling with the first and second sutures to spread a supporting force of the first and second sutures over a greater area.

18. A device for suspending, stabilizing, and/or slightly compressing a bodily structure, the device comprising:

a delivery needle comprising an elongate cannula with a proximal end, a distal end, and a body portion;

a trocar disposed at the distal end of the delivery needle;

a stylet comprising an elongate rod for being matingly received into the cannula of the delivery needle; and a support comprising an anchor toggle and elongate first and second sutures wherein each of the first and second sutures has a first end secured to the anchor toggle and a free second end wherein each of the first and second sutures extend from a central portion of the anchor toggle;

a longitudinal slot formed in the delivery needle wherein the longitudinal slot begins at the distal end of the cannula, communicates longitudinally along the cannula, and terminates a given distance away from the distal end of the cannula whereby the support can be retained within the distal end of the delivery needle with the anchor toggle at least partially disposed in the distal end of the delivery needle and the first and second sutures protruding from the slot;

wherein the body portion of the delivery needle has a curve therein, wherein the trocar is angled such that the trocar has a distal tip and a proximal base with the distal tip of the trocar disposed on an outside of the curve in the delivery needle, and wherein the slot is disposed in the base of the trocar and on an inside of the curve whereby the first and second sutures protrude through the slot on the inside of the curve;

whereby the delivery needle and the stylet can be used to deploy the anchor toggle remotely in a desired location in a body to provide support for the first and second sutures and thereby to support, stabilize, and/or compress a bodily structure.

19. The device of claim 18 further comprising a means for indicating a depth to which the delivery needle has been inserted into a patient's body.

20. The device of claim 19 wherein the means for indicating the depth to which the delivery needle has been inserted comprises a series of depth calibration markings disposed along the body portion of the delivery needle wherein the series of depth calibration markings comprise a plurality of coded stripes wherein different numbers of stripes indicate different depths.

21. A method for the correction of urinary incontinence without percutaneous incision, the method comprising the steps of:

providing a delivery needle comprising an elongate cannula with a proximal end, a distal end, and a body portion;

providing a stylet comprising an elongate rod for being matingly received into the cannula of the delivery needle;

providing a urethrovesical support comprising an anchor toggle with at least an elongate first suture with a proximal end fixed to the anchor toggle and a free distal end;

inserting the distal end of the elongate cannula of the delivery needle partially into a perineum of a patient's body that has a bladder structure with a bladder, a urethrovesical junction, and a urethra;

passing the distal end of the cannula through the perineum wall, across the space of the Retzius behind the symphysis pubis, and then to a desired supporting location but not so far that the distal end of the cannula or the anchor toggle creates a percutaneous incision;

inserting the anchor toggle of the urethrovesical support at least partially into the cannula of the delivery needle;

inserting the elongate rod of the stylet into the proximal end of the cannula of the delivery needle;

deploying the anchor toggle of the urethrovesical support by sliding the elongate rod of the stylet increasingly deeper into the cannula of the delivery needle at least until the distal end of the elongate rod drives the anchor toggle out of the distal end of the cannula and into the desired supporting location;

removing the elongate cannula of the delivery needle from the patient's body thereby leaving the anchor toggle in position and leaving the at least one elongate first suture in place; and coupling the at least one suture to the bladder structure of the patient's body thereby providing support, compression, and/or stabilization to the bladder structure with the anchor toggle acting as a supporting anchor and the at least one suture acting as a supporting line;

whereby urinary stress incontinence in the patient can be corrected.

22. The method of claim 21 wherein the step of providing the urethrovesical support comprises providing an anchor toggle and elongate first and second sutures wherein each of the first and second sutures has a first end secured to the anchor toggle and a free second end wherein each of the first and second sutures extend from a central portion of the anchor toggle.

23. The method of claim 22 wherein the step of coupling the at least one suture to the bladder structure of the patient's body comprises the steps of disposing the first suture to a first side of the bladder structure, disposing the second suture to a second side of the bladder structure, and securing the second end of the first suture relative to the second end of the second suture thereby to provide support, compression, and/or stabilization to the bladder structure.

24. The method of claim 23 wherein the step of securing the second end of the first suture relative to the second end of the second suture comprises tying the second ends of the first and second sutures directly together.

25. The method of claim 23 further comprising the step of providing a sling for coupling with the first and second sutures to spread a supporting force of the first and second sutures over a greater area.

26. The method of claim 21 wherein the step of passing the distal end of the cannula through the perineum wall, across the space of the Retzius behind the symphysis pubis, and then to a desired supporting location comprises passing the distal end of the cannula through the perineum wall, across the space of the Retzius behind the symphysis pubis, and then until the distal end of the cannula has pierced a rectus abdominus of the patient thereby carrying the anchor toggle through the rectus abdominus but not so far that the distal end of the cannula or the anchor toggle creates a percutaneous incision.

27. The method of claim 21 wherein the step of providing the delivery needle comprises the step of providing a delivery needle with a longitudinal slot formed therein wherein the longitudinal slot begins at the distal end of the cannula, communicates longitudinally along the cannula, and terminates a given distance away from the distal end of the cannula, wherein the step of inserting the anchor toggle at least partially into the cannula of the delivery needle is performed prior to the step of inserting the distal end of the elongate cannula of the delivery needle partially into the perineum of the patient's body, and wherein the step of inserting the anchor toggle at least partially into the cannula of the delivery needle comprises disposing the anchor toggle at least partially in the distal end of the delivery needle with the first and second sutures protruding from the longitudinal slot.

28. The method of claim 27 wherein the step of providing the delivery needle comprises the step of providing a delivery needle with a curve therein, with the slot disposed on an inside of the curve whereby the first and second sutures protrude through the slot on the inside of the curve, and a trocar disposed at the distal end of the delivery needle with the trocar angled such that the trocar has a distal tip on an outside curve of the delivery needle and a proximal base and with the slot disposed adjacent to the base of the trocar.

* * * * *